United States Patent
Hargittai

(10) Patent No.: US 9,700,421 B2
(45) Date of Patent: Jul. 11, 2017

(54) PROSTHETIC DEVICES AND IMPLANTS

(71) Applicant: Orthomed (UK) Limited, Edgerton, Huddersfield (GB)

(72) Inventor: Tamas Hargittai, Orpington (GB)

(73) Assignee: ORTHOMED (UK) LIMITED, Edgerton, Huddersfield (GB)

( * ) Notice: Subject to any disclaimer, the term of this patent is extended or adjusted under 35 U.S.C. 154(b) by 0 days.

(21) Appl. No.: 14/380,856

(22) PCT Filed: Feb. 21, 2013

(86) PCT No.: PCT/GB2013/050418
§ 371 (c)(1),
(2) Date: Aug. 25, 2014

(87) PCT Pub. No.: WO2013/124657
PCT Pub. Date: Aug. 29, 2013

(65) Prior Publication Data
US 2015/0032219 A1  Jan. 29, 2015

(30) Foreign Application Priority Data
Feb. 24, 2012 (GB) .................................. 1203340.3

(51) Int. Cl.
*A61F 2/38* (2006.01)
*A61F 2/30* (2006.01)

(52) U.S. Cl.
CPC ............ *A61F 2/3877* (2013.01); *A61F 2/38* (2013.01); *A61F 2002/30703* (2013.01)

(58) Field of Classification Search
CPC ..................................... A61F 2/38–2002/3895
See application file for complete search history.

(56) References Cited

U.S. PATENT DOCUMENTS

| 4,903,691 | A | 2/1990 | Heinl |
| 5,609,642 | A * | 3/1997 | Johnson ............... A61B 17/155 606/88 |
| 5,690,631 | A | 11/1997 | Duncan et al. |
| 6,171,340 | B1 | 1/2001 | McDowell |
| D469,875 | S | 2/2003 | Bryant et al. |
| D480,141 | S | 9/2003 | Benirschke et al. |
| 7,229,445 | B2 | 6/2007 | Hayeck et al. |

(Continued)

FOREIGN PATENT DOCUMENTS

| EP | 1 864 629 A2 | 12/2007 |
| FR | 2 440 185 A1 | 5/1980 |

(Continued)

OTHER PUBLICATIONS

Intellectual Property Office Search Report for Application No. GB1303041.6 dated Jul. 8, 2013; 1 page.

(Continued)

*Primary Examiner* — Thomas J Sweet
*Assistant Examiner* — Daniel Bissing
(74) *Attorney, Agent, or Firm* — Howard & Howard Attorneys PLLC

(57) ABSTRACT

A trochlear ridge prosthesis includes a curved section, the curved section having a span (RS) and a height (RH) above the span, the ratio of the height to the span being in the range 0.15 to 0.35, and a tail extending from a proximal end of the curved section.

13 Claims, 16 Drawing Sheets

(56) References Cited

U.S. PATENT DOCUMENTS

| | | |
|---|---|---|
| 7,846,189 B2 | 12/2010 | Winquist et al. |
| D648,027 S | 11/2011 | Vancelette et al. |
| 8,234,097 B2 * | 7/2012 | Steines .............. A61B 17/1675 128/898 |
| D735,861 S | 8/2015 | Embleton et al. |
| 2006/0167459 A1 | 7/2006 | Groiso |
| 2008/0195149 A1 | 8/2008 | Burke |
| 2010/0121389 A1 * | 5/2010 | Librot ................ A61B 17/1764 606/86 R |
| 2010/0131065 A1 | 5/2010 | Burke |

FOREIGN PATENT DOCUMENTS

| | | |
|---|---|---|
| FR | 2440185 A1 * | 5/1980 |
| FR | 2 682 589 A1 | 4/1993 |
| GB | 2 137 098 A | 10/1984 |
| GB | 2 414 674 A | 12/2005 |
| GB | 2 449 334 A | 11/2008 |
| KR | 2007 0060623 A | 6/2007 |
| WO | WO 02 17803 A2 | 3/2002 |
| WO | WO 2007 044391 A2 | 4/2007 |

OTHER PUBLICATIONS

E.W. Winstanley and L.N. Gleeson, "Prosthetic trochlear ridge for treatment of patellar luxation in a calf", Journal of the American Veterinary Association, vol. 164, Issue 8, Apr. 1974, pp. 807-808, U.S. National Library of Medicine Accession; 3 pages.

Intellectual Property Office Search Report for Application No. GB1303041.6 dated Sep. 16, 2013; 1 page.

Patent Cooperation Treaty International Search Report for Application No. PCT/GB2013/050418 dated Jul. 29, 2013; 6 pages.

English language abstract and machine-assisted English language translation of FR 2 440 185 A1 extracted from on www.espacenet.com on Oct. 13, 2014; 8 pages.

English language abstract and machine-assisted English language translation of FR 2 682 589 A1 extracted from on www.espacenet.com on Oct. 13, 2014; 5 pages.

English language abstract and machine-assisted English language translation of KR 2007 0060623 A extracted from on www.espacenet.com on Oct. 13, 2014; 5 pages.

* cited by examiner

RS : 1.45 cm
0.37 cm

PROSTHETIC DEVICES AND IMPLANTS

RELATED APPLICATION

This application is the National Stage of International Patent Application No. PCT/GB2013/050418, filed on Feb. 21, 2013, which claims priority to and all the advantages of Great Britain Application No. 1203340.3, filed on Feb. 24, 2012, the content of which is incorporated herein by reference.

The present invention relates to a prosthetic trochlear ridge for canines, felines and other four-legged animals, and to other implants for use with mammals, and to methods of installing them.

Patellar luxation is a significant problem for dogs and cats (the terms "dog" and "cat" in this specification including all canines and all felines respectively and not being limited to domesticated animals).

FIG. 1A shows a side view and FIG. 1B shows a front view of a canine knee joint comprised of the proximal tibia and the distal femur in a well animal. The left hand drawing of FIG. 2 is another front view of the knee joint and FIG. 3 is an end view of the femur showing the trochlea and the patella. The left hand drawing of FIG. 2 shows the arrangement of the patella 1 and the patellar ligament 3 tracking well in the trochlear groove formed in the femoral condyle 2. The bottom (distal end) of the patellar ligament 3 is joined to the tibia at the tibial crest 4. As the left hand drawing in FIG. 2 and FIG. 3 show, the trochlea comprises two trochlear ridges 110 with the trochlear groove 120 between them. The patellar ligament runs along the groove and the patella itself is disposed between the ridges. Proper alignment is critical to normal patella tracking. In particular, the patella normally slides up and down on the trochlea in a central position and is responsible for the development of the trochlear groove with adequate depth.

Patellar luxation is the misalignment of the patella with the trochlear groove so the patella and patellar ligament do not track properly within it. Thus, the middle drawing in FIG. 2 shows medial luxation, in which the patella 5 is disposed toward the inside of the knee joint and the right hand drawing in FIG. 2 shows lateral luxation, in which the patella 6 is disposed toward the outside of the joint. Each type of misalignment can cause pain, an awkward gait and varying degrees of lameness, which can entail a series of secondary health issues.

Patella luxation typically occurs as a congenital defect in animals, although it can sometimes also occur as the result of trauma. Medial luxation is more common in smaller breeds, whereas lateral luxation is more common in larger breeds. Luxation itself can cause significant pain and discomfort due to an abnormal gait. However, where it results from a congenital defect or trauma in a young animal, the forces that are abnormally directed due the luxation can result in further and even worse deformations of the femur and tibia as the animal grows. Moreover, failure of the patella and ligament to track in the groove, or riding on a trochlear ridge, can cause a ridge to become worn down or flattened and failure of the groove to form to a proper depth. This can result in exposure of sub-chondral bone on the ridge, which can be a significant source of pain.

Difficulties can also arise where the patella lies proximal to the trochlea groove when the leg is extended, due to a long patella ligament so the trochlear ridges fail to provide an effective medial or lateral barrier, enabling easy patella dislocation in an animal that is predisposed to it due to a conformational abnormality.

It is strongly preferable to correct for patellar luxation at an early stage as possible, to avoid bone deformation as the animal grows, to promote correct formation of the trochlear groove and to prevent deterioration as a result of the abnormal direction of forces exerted by the misaligned quadriceps mechanism. Untreated, patellar luxation may lead to osteoarthritis and progressive degenerative joint disease.

Existing treatments include tibial tuberosity transposition in which the tibial crest is repositioned so that the patellar ligament and patella are properly aligned with the groove; trochlear groove deepening (sulcoplasty) by using a saw and sometimes a chisel and mallet to cut a deeper groove in the trochlea; lateral imbrication of the joint capsule; medial release of the femoropatellar ligament correctional osteotomy of the distal femur to help realign the trochlear groove with the patella; and the use of a full trochlear prosthesis in which the entire trochlea is sawn off from the femoral condyle and replaced with a prosthesis, the prosthesis providing both trochlear ridges and a prosthetic trochlear groove.

Usually a combination of at least two of these surgical techniques is applied in treatment, and at least one of them always involves an osteotomy (sawing the bone). Deepening the trochlear groove by sawing the bone (sulcoplasty) is almost always desirable as is too shallow almost by definition (except in traumatic luxations which are the minority of cases and uncommon), therefore sulcoplasty is a major part of proper surgical treatment of patella luxations.

However, sulcoplasties have various difficulties in that they are traumatic (sawing and chiseling of bone); they provide inconsistent results, particularly with respect to groove depth; they involve comparatively large surgical risks; art inadequate depth is achieved at the proximal end of the groove, where most luxations occur; they are time consuming; and, most of all, they are not appropriate for young immature animals (clue to a still active growth plate which, if disturbed by surgery, can result in abnormal growth and even worse deformities).

More generally, there is a problem that where implants are attached to bones of young animals and children, there is a problem that the implant must not span a growth plate within the bone to allow for normal growth of the patient This limits the effectiveness of such implants.

Accordingly, it is an object of the present invention to provide an improvement in the correction of patellar luxation and in implants generally.

According to a first aspect of the present invention, there is provided a trochlear ridge prosthesis comprising a curved section, the curved section having a span RS and a height RH above the span, the ratio of the height to the span RH/RS being in the range 0.15 to 0.35.

The inventor has recognised that patellar luxation can be treated by providing a trochlear ridge prosthesis and attaching it an affected trochlea ridge of an animal. The inventor has further recognised that the geometry of the trochlea is substantially constant in canines, felines and other four-legged animals, allowing prostheses of constant geometry and varying dimensions to be cheaply produced and fitted.

Preferably, the ratio is within the range 0.2 to 0.28, more preferably within the range 0.23 to 0.27 and most preferably substantially 0.25.

It is preferred that the prosthesis further comprises a tail extending from a proximal end of the curved section.

In another aspect of the invention, there is provided a trochlear ridge prosthesis comprising a curved section and a tail extending from a proximal end of the curved section.

Preferably, the length of the tail in either aspect is between 1 and 1.5 times the span.

The provision of the tail improves the fitting of the prosthesis to the bone and/or further assists in hindering subsequent luxation, particularly in cases of Patella Alta.

It is preferred that there is a slot extending longitudinally along the tail for a fixing means for fixing the prosthesis to an animal, whereby the fixing means can slide in the slot.

Where the prosthesis is fixed to span a growth plate in an immature animal, the fixing means can slide in the slot as the animal grows. Thus, the prosthesis can be fitted to young animals, which has significant benefits.

In a preferred arrangement, the fixing means is a screw and the slot includes a countersink for accommodating the head of the fixing means. This allows for the prosthesis to have a smooth contour when fitted, thereby reducing irritation to the animal.

Preferably, the prosthesis comprises a hole in the distal end of the curved section for a fixing means for fixing the prosthesis to an animal.

Preferably, the prosthesis comprises at least two holes for fixing means, the two holes being disposed so that the longitudinal axes of the respective fixing means are not disposed in a plane. This allows for superior fixing of the prosthesis in situ and improved resistance to lateral forces.

Preferably, an underside of the prosthesis is concave. More preferably, an upper side of the prosthesis is convex, the curvature of the concave underside side being shallower than the curvature of the convex upper side.

In a preferred arrangement, the medial and lateral sides of the prosthesis are sloped, the medial slope being steeper than the lateral slope. The steeper medial slope allows the prosthesis to hold the patella in place, while the shallower lateral side allows the patella to be more easily slid into to place in the event of subsequent luxation, as well as providing a more comfortable geometry and reducing irritation.

Preferably, the prosthesis has a substantially smooth outer surface.

It is preferred that the prosthesis is for use with at least two fixing means for fixing the prosthesis to a trochlear ridge, wherein the prosthesis is adapted so that said two fixing means are able to move relative to one another in situ. This allows the prosthesis to be fitted across a growth plate without hindering growth.

According to a further aspect of the present invention, there is provided a kit comprising a trochlear ridge prosthesis as described above and at least one fixing means.

It is preferred that the kit comprises one or both of a cancellous screw for mounting a distal end and a conical screw for mounting a proximal end.

According to a still further aspect of the invention, there is provided a method of treating petellar luxation, comprising:

measuring a ridge span of a trochlear ridge;
selecting an appropriate size of trochlear ridge prosthesis based on the measurement; and
fixing a trochlear ridge prosthesis of the appropriate size to the trochlear ridge.

It is preferred that the trochlear ridge prosthesis is a trochlear ridge prosthesis as described above.

Preferably, the step of fixing comprises attaching the prosthesis to span a growth plate using at least two fixing means, the two fixing means being fixed to opposite sides of the growth plate, whereby the two fixing means are able to move relative to one another in at least one direction.

Preferably, an elongated slot is provided in either the prosthesis or a said fixing means, the other of the prosthesis and the said fixing means protruding through the slot whereby it can slide along the slot as the bone grows.

According to a yet further aspect of the invention, there is provided an implant adapted to span a growing part of—animal anatomy in situ using at least two fixing means, the two fixing means being attached to opposite sides of the growing part, whereby the two fixing means are able to move relative to one another in at least one direction.

It is preferred that the implant comprises an elongated slot through which a said fixing means is able to protrude, whereby the fixing means can slide along the slot as the growing part grows.

Preferably, the implant comprises a protrusion adapted to protrude through an elongated slot provided in a said fixing means, whereby the protrusion can slide along the slot as the growing part grows.

According to a still further aspect of the present invention, there is provided a kit comprising an implant as described above and at least one of the two said fixing means.

Preferably, at least one of the fixing means is a screw or a pin.

Embodiments of the present invention will now be described by way of further example only and with reference to the accompanying drawings, in which.

Figure 5:
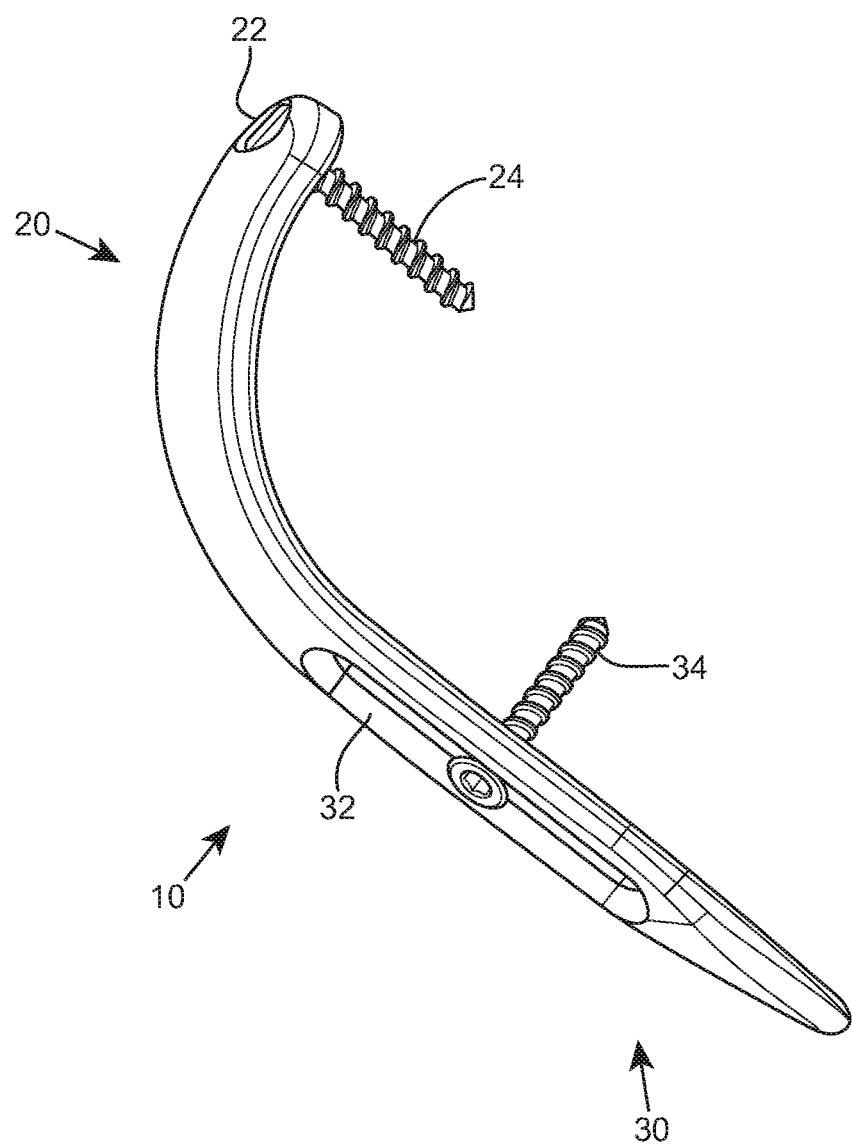
Figure 6:
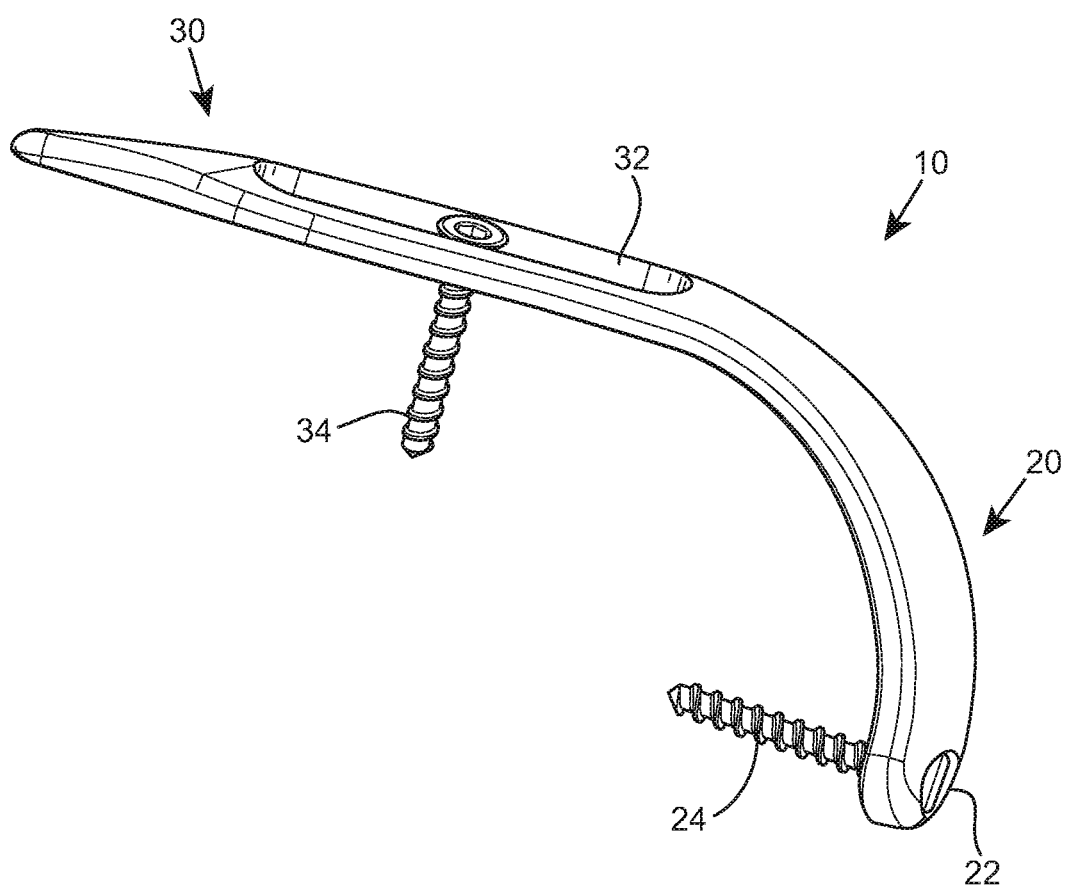
Figure 7:
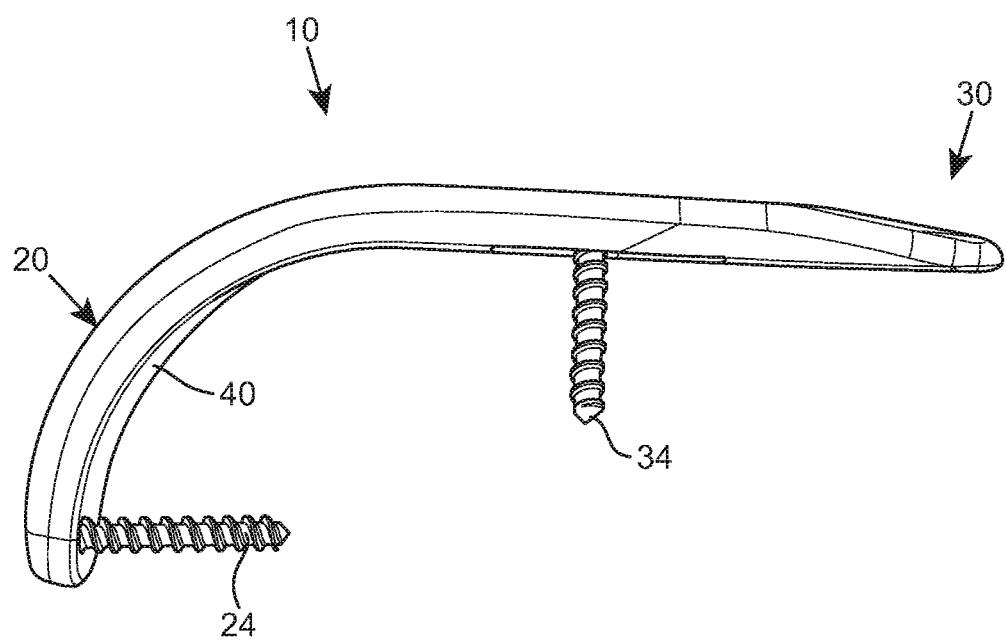
Figure 8:
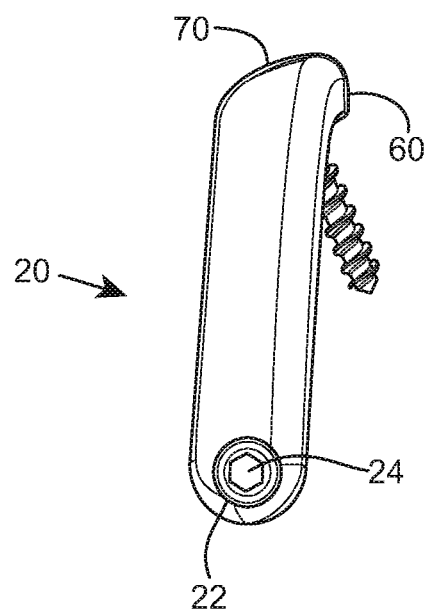
Figure 9:
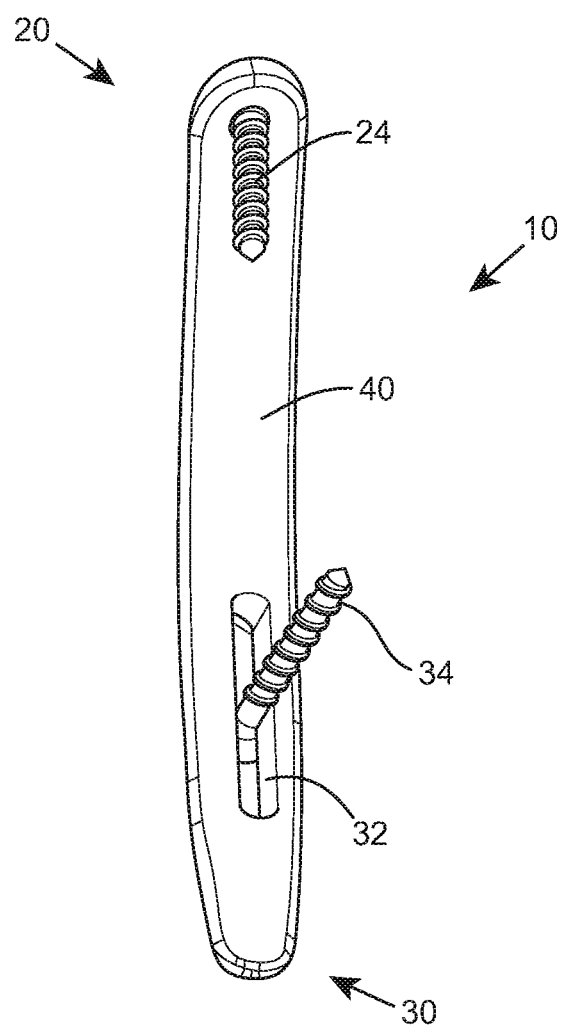
Figure 10:
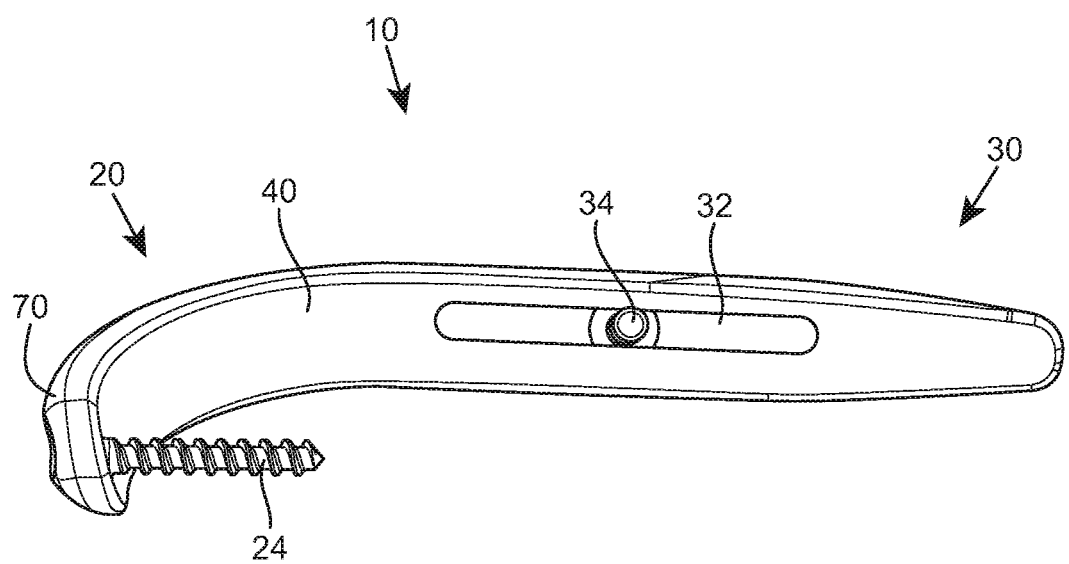
Figure 11:
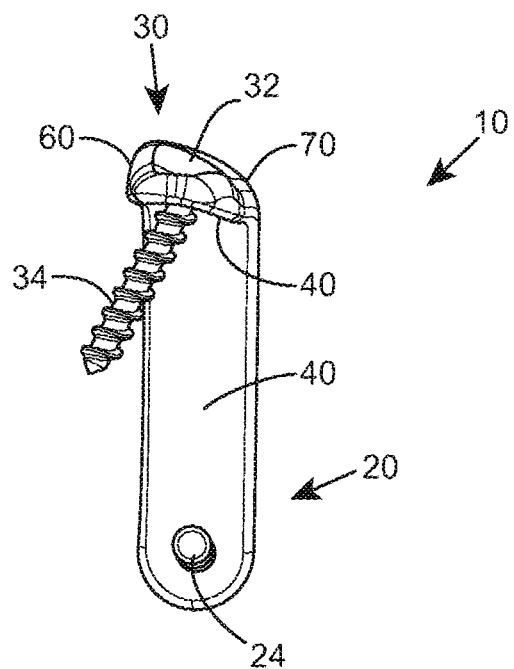
Figure 12:
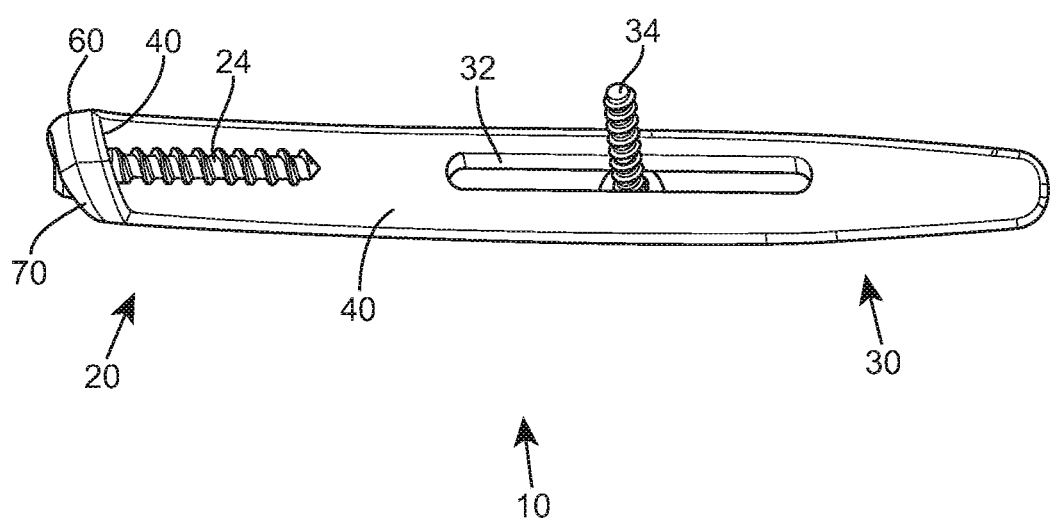
Figure 13:
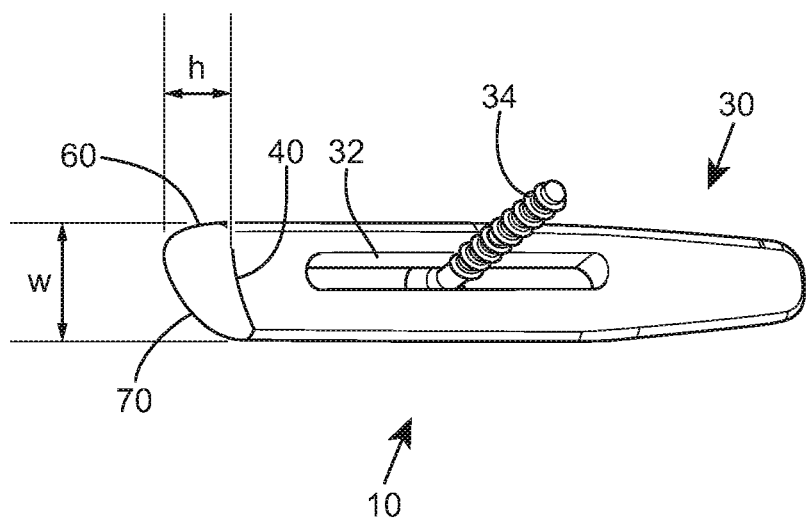
Figure 14:
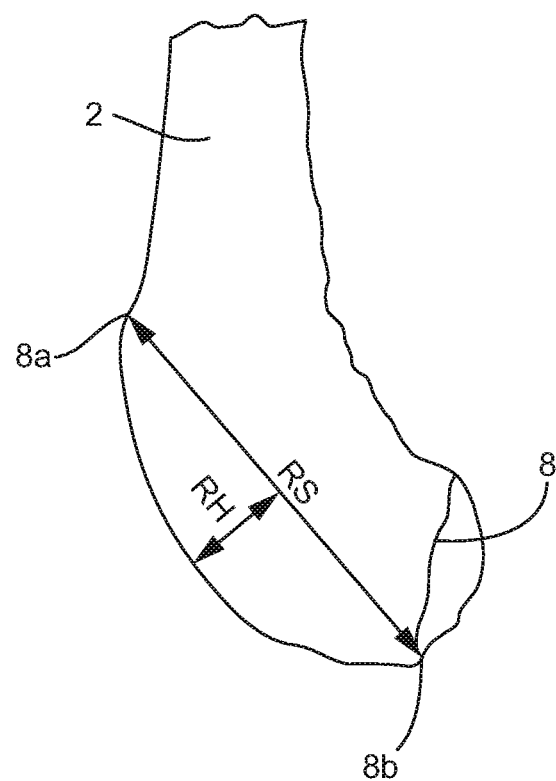
Figure 15:
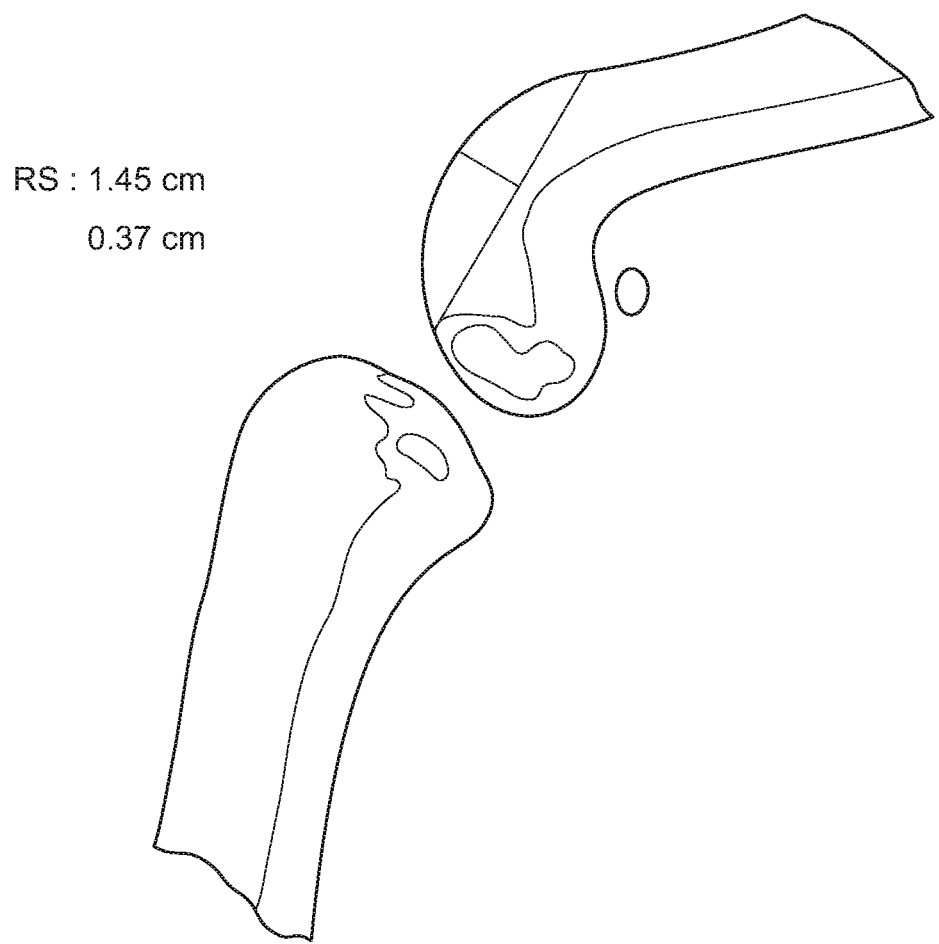

FIG. 5 is a perspective view of the prosthesis;
FIG. 6 is a lateral side view of the prosthesis;
FIG. 7 is a medial side view of the prosthesis;
FIG. 8 is a plan view over the distal end of the prosthesis;
FIG. 9 is an underside perspective view of the prosthesis;
FIG. 10 is an underside plan view over the proximal end of the prosthesis;
FIG. 11 is an underside p (an view over the distal end of the prosthesis;
FIG. 12 is a front view of the distal end of the prosthesis also showing the underside of the proximal end;
FIG. 13 is a cross sectional view of the prosthesis;
FIG. 14 is a cross-sectional view of a canine femur; and
FIG. 15 is an X-ray of a canine femur.

Figures 1A, 1B:
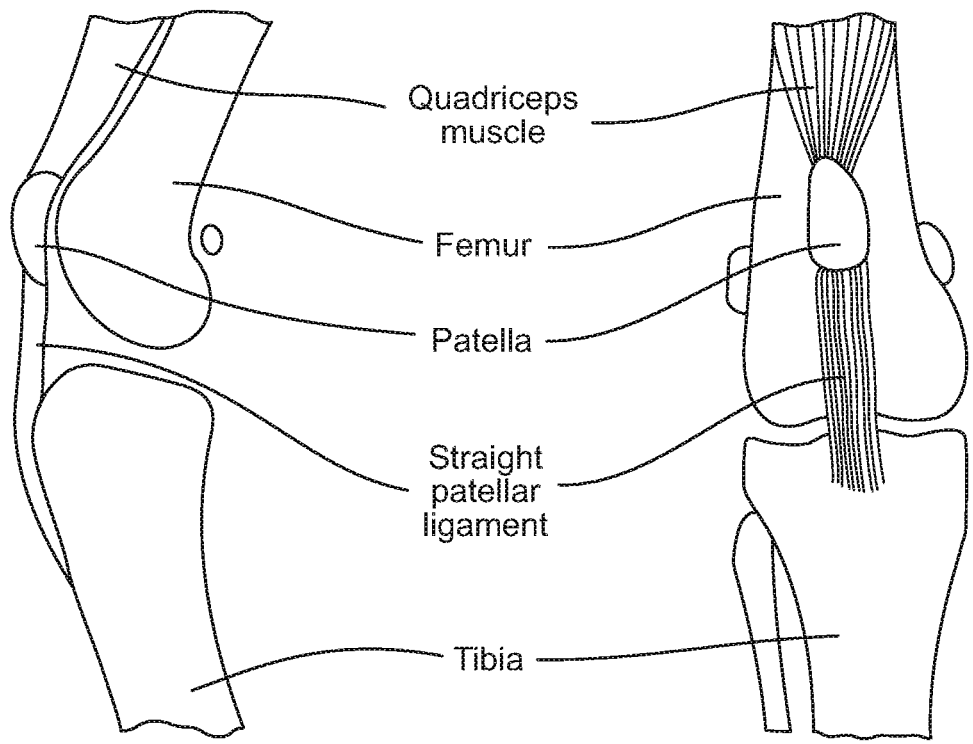
FIG. 1A is a side view of a well-aligned canine knee joint and FIG. 1B is a front view of the joint.
Figure 2:
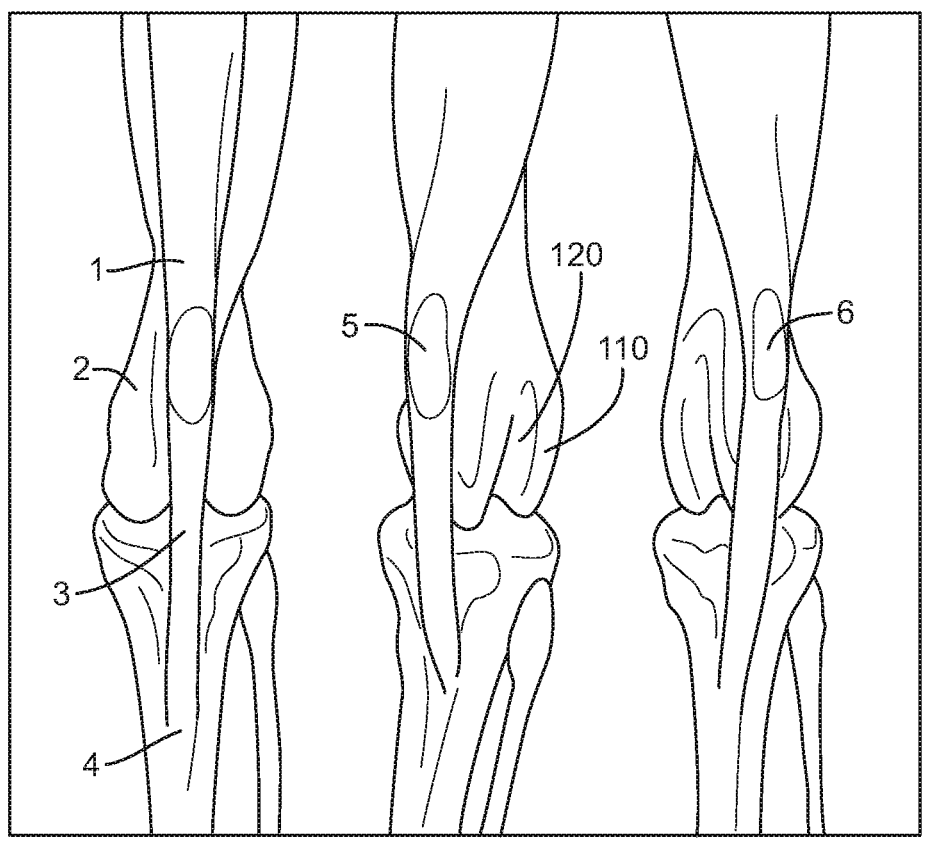
FIG. 2 shows views respectively from left to right of a well aligned canine knee joint, medial luxation of the patella and lateral luxation of the patella.
Figure 3:
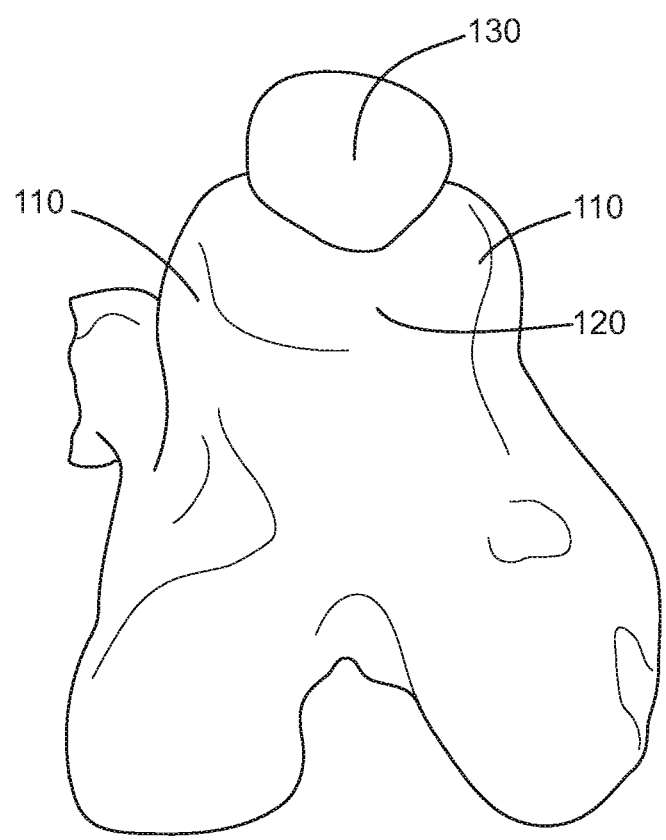
FIG. 3 shows a front end view of a canine trochlea and patella.
Figure 4A:
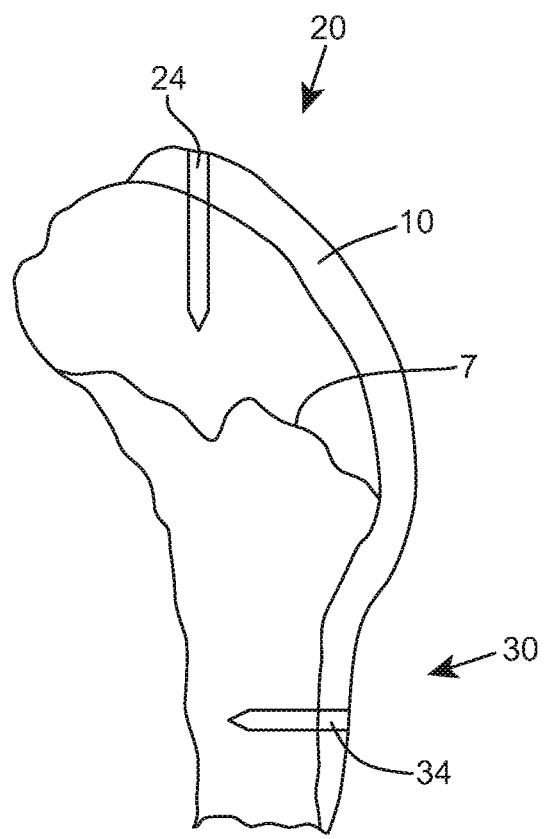
FIG. 4A shows the side of a femoral condyle showing a prosthesis according to the present invention attached to the femur.

In one embodiment, the present invention provides a prosthetic trochlear ridge for canines and felines. Thus, FIGS. 4A and 48 show a canine femur 2 and the prosthetic ridge 10 having a distal end 20 arid a proximal end 30 fixed to the femur 2 by means of screws 24, 34. The prosthesis 10 has complex geometry and various views of it are shown in the figures to aid understanding. The prosthesis 10 acts as prosthetic trochlear ridge and causes the patella and the patellar ligament to run in the trochlear groove 120. Key features of the prosthesis 10 will now be described.

As shown in the figures, the distal end 20 forms a curved section and the proximal end 30 forms a tail which extends tangentially from the curved section. The curved section is shaped to follow the curvature of the condyle and the tail is shaped to fit to the femur extending up from the condyle. As FIG. 4A shows, the prosthesis 10 spans over the growth plate 7.

The distal end 20 includes a round hole 22 through which a distal screw 24 penetrates. By contrast, the proximal end 30 includes a slot 32 extending longitudinally along the tail through which a proximal screw 34 penetrates. The round hole 22 is arranged so that the distal screw 24 extends from the end of the femur in the direction of the longitudinal axis of the femur. By contrast, the slot 32 is arranged so that the proximal screw 34 extends at approximately 90 degrees to the screw 24 when viewed from the lateral or medial side of the prosthesis 10 (see FIGS. 6 and 7). Moreover, the round hole 22 and the slot 32 are arranged so that the longitudinal axes of the screws do not lie in the same plane or in parallel planes. Rather, as illustrated in FIGS. 8, 9, 11 and 12, for example, the slot 32 is arranged so that the longitudinal axis of the proximal screw 34 is angled in the medial direction. Preferably the slot 32 is arranged so that the proximal screw is angled at 25° to the distal screw. In this manner, the screws 24, 34 strongly anchor the prosthesis 10 to the femur 2 and provide against both lateral and longitudinal movement of the prosthesis 10 in situ.

Preferably, the distal screw 24 is of cancellous type and/or the proximal screw is of cortical type. Moreover, either or both of the screws may include added surfacing or gaps to aid osteointegration of the screws with the bone. The proximal screw 34 need not be threaded along its entire length, and a smooth, non-threaded part may extend down from the head of the screw for a distance equal to the height of the prosthesis. This screw may be used in immature animals to enable the screw to slide within the slot of the sliding hole with greater ease as the animal grows, as discussed in more detail below.

The prosthesis 10 is made of an implant grade plastic, such as ultra-high-molecular-weight polyethylene (UHMWPE), with at least some flexibility and/or elasticity to enable a snug fit and to enable the prosthesis to change shape as the bone grows when implanted in an immature animal. Alternatively, a fixed-shape, non-flexible prosthesis can be also applied in adult animals. The screws 24, 34 are made of any suitable biocompatible material, although titanium is preferred.

The prosthesis 10 has a smooth contour all around with no sharp or rough edges. Preferably, it is made of a block design and can be moulded as one seamless part. It is provided with an ultra smooth finish for substantially frictionless sliding of the patella and the patellar ligament. Both the round hole 22 and the slot 32 include a countersunk portion to accommodate the head of the respective screw 24, 34. Thus, the screw heads do not protrude above the contour of the prosthesis 10 and do present sharp edges in use. Consequently, there are no pressure points and irritation of Overlying soft tissue is minimised.

Figure 4B:
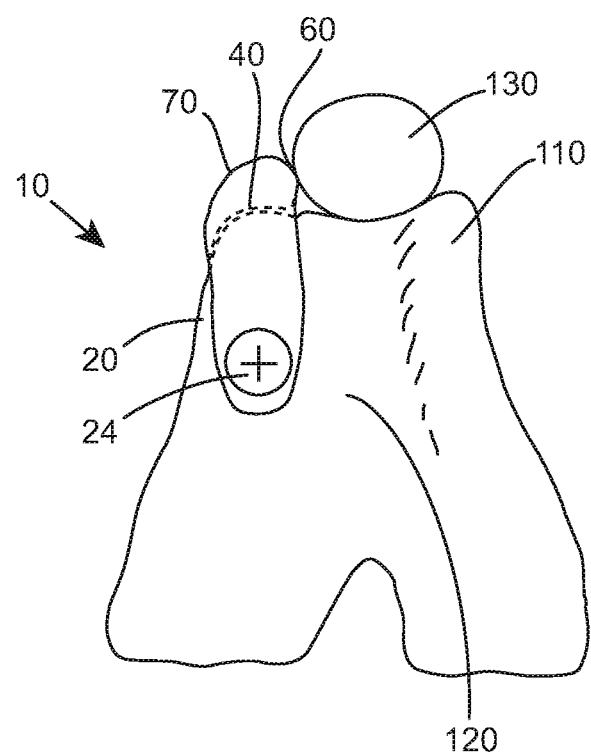
FIG. 4B shows the front of a femoral condyle showing a prosthesis according to the present invention attached to the femur, in which the dotted lines illustrate part of the prosthesis and the trochlear ridge in cross-section.

A cross section of the prosthesis 10 is shown in FIG. 4B and FIG. 13. As these figures show, the cross-section has substantially three sides, a medial side 60, a lateral side 70 and an underside 40.

The underside 40 is concave and approximately abuts the trochlear ridge 110 in situ. The prosthesis 10 is fitted in "lag" fashion by both screws, with the diameter of the round hole 22 and the elongated slot 32 being the same as the diameter of the threads of the respective screws 24, 34, and both screws 24, 34 engage only the bone and not the prosthesis, thereby pulling the prosthesis down onto the surface.

Although not necessary, in alternative embodiments the prosthesis 10 is designed with geometry such that it can be ensured that the curvature of the concavity before the prosthesis 10 is fitted is greater than the curvature of the corresponding convex portion of the trochlear ridge 110 that it abuts. In general, this is easily achieved where an abnormal trochlear ridge 110 has been worn down and is flatter than normal. However, it can be ensured by providing different prostheses 10 of the same size and shape but with different degrees of curvature of the underside 40. Since the prosthesis 10 has some degree of elasticity/flexibility, when the prosthesis 10 is fitted and is pulled down onto the surface of the bone, the underside moulds so that it conforms well to the shape of the bone.

As shown in FIGS. 4A and 13, the side edges of the underside 40 are not level. Rather, although the side edges are preferably both lower than the top of the concavity, the medial edge of the underside is higher than the lateral edge. This also assists shaping of the prosthesis 10 to the trochlear ridge 110.

By contrast, the medial side 60 and lateral side 70 form a curved convex surface. The medial side 60 and the lateral side 70 slope downwards from the top of the prosthesis 10 to opposite side edges of the underside 40. The medial side 60 slopes more steeply than the lateral side 70. In situ, the medial side 60 faces the patella 130 and the steepness of the slope helps maintain the patella 130 in the trochlear groove 120. By contrast, the lateral side 70 faces away from the patella 130. In the event that the patella is luxated after the prosthesis 10 has been fitted, the smooth, gentle slope of the lateral side 70 allows the patella 130 and the patellar ligament to be easily slid over the prosthesis 10 back into the groove 120.

It should also be noted that the prosthesis 10 tapers off—that is, becomes thinner—towards the ends at both the distal and proximal ends 20, 30. The tail on the proximal end 30 is shaped to end in a round point. This allows the tail to be more easily tucked under the muscles when the prosthesis 10 is fitted.

Note that there are no sharp edges between any of the underside 40, medial side 60 and lateral side 70.

The present invention is predicated, in part, on the recognition by the inventor that the geometry of the trochlea is substantially constant irrespective of the breed and size of dog. It is expected that this will be the case across all canines. It is further expected that felines and other four-legged animals will have a substantially constant trochlea geometry. FIGS. 14 and 15 show how the span RS of a trochlea ridge can be determined by measuring in a straight line from opposite end points of the trochlear ridge, specifically from the proximal point of the cartilage on the trochlear ridge 8a to the level of the condylar notch 8b. Similarly, the ridge height RH can be determined by measuring the distance from the middle of the ridge span to the top of the troch ridge, with the RH being perpendicular to the ridge span RS.

The ridge span RS measurement is easy for veterinarians to determine from a single x ray of the knee (stifle) joint. In particular, FIG. 14 shows a line extending across the condyle at the distal end, which represents the intercondylar depth. This line can also be seen on the mediolateral radiograph shown in FIG. 15. The condylar notch is in the middle of the distal femur and the location of the condylar notch corresponds to where this line begins. Thus, the ridge span RS is measured in a mediolateral radiograph of the stifle joint from where this line originates to the proximal extent of the trochlear cartilage, where the curvature of the trochlea ends.

Analysis of a large number of X-rays (over 40) of dogs of different sizes and breeds shows that the ratio RH:RS of the ridge height RH to the ridge span RS (RH/RS) is substantially constant at 0.25-0.28. This geometry has not previously been recognised. However, the inventor's insight with respect to this geometry allows prostheses 10 according to the present invention to be mass-produced in different sizes.

Specifically, if the ridge span RS is known, then the size and shape of the femoral condyle can be predicted with confidence and different prosthesis sizes can be accurately made in advance for different sizes of dog. Thus, the veterinary surgeon is able to determine the required size of implant based on one measurement on one X-ray only.

It should be noted that, as shown in FIG. 4A, the prosthesis 10 spans the growth plate 7. In young animals, it is strongly preferable that the screws do not penetrate the growth plate 7 to ensure proper growth of the femur. Although the distal screw 24 extends towards the growth plate 7 when the prosthesis 10 is fitted, the inventor has further recognised that the ratio (distance:RS) of the ridge span RS to the distance that the distal screw 24 may penetrate before it touches the growth plate 7 is relatively constant at around 0.4 (distance to growth plate/RS=APPROX 0.4). Accordingly, the appropriate size screw 24 may be provided with each size of prosthesis 10 without the need for the surgeon to measure this distance. It is therefore possible to provide various sized kits, each comprising the prosthesis 10 (the main body) and screw 24 of the correct size, and for the surgeon to select the correctly sized kit based on one measurement (RS) on one X-ray only. The length of the proximal screw 34 needs to be determined by the surgeon during surgery, using a depth gauge after drilling the hole, which is a well established routine in orthopaedic surgery.

The prosthesis may be made with an RH:RS ratio of 0.15 to 0.35, preferably 0.2 to 0.28, more preferably 0.23 to 0.27, and most preferably 0.25, where the dimensions of the ridge span RS and the ridge height RH apply to the underside dimensions of the curved distal section 20, and in particular the deepest part of the concavity of the underside 40 in the distal section 20. Although the RH:RS ratio in animals is substantially constant at 0.25-0.28, it is preferred to provide the prosthesis 10 with a lower RH:RS ratio. With this under-curvature, the elasticity of the prosthesis 10 allows it to be snugly fitted against the trochlear ridge in lag fashion.

The length TL of the tail can be varied as required. For reasons that will become apparent from the following discussion, the tail length TL is based on the growth of a puppy (or other infant mammal) to adulthood. However, in the present embodiment it is 1.25×RS. Accordingly, a typical prosthesis 10 according to the present invention will have a ridge span RS of 20 mm, a ridge height RH of 5 mm arid a tail length of 25 mm.

The height h of the prosthesis from the bottom of the concavity on the underside 40 to the highest point as shown in FIG. 13, can be based on the constant geometry of the joint. In particular, it is preferably determined as 30-50% and more preferably 30-40% of the height of the patella. In the typical prosthesis 10 discussed above, the height is 3 mm.

Table 1 below shows preferred dimensions for kits comprising of varying sizes, each comprising the prosthesis 10 and the proximal and distal screws 24, 34 In each case, the ridge height RH=0.25 RS and tail length=1.25 RS. All dimensions are given in mm. However, the present invention is not limited to these specific dimensions or combinations of prosthesis 10, distal screw 24 and proximal screw 34 In particular, as discussed below, the dimensions of the proximal (sliding) screw 34 are not fixed although it is expected that further clinical experience will enable a more definitive determination of the dimensions of the proximal (sliding) screw 34. Accordingly, it is currently preferred that a kit is provided either without a proximal (sliding) screw 34 or with a variety of sizes of proximal (sliding) screw 34.

As will be evident from the foregoing, the prosthesis 10 has an asymmetric geometry. One aspect of this asymmetry is manifested in a twist between the proximal and distal ends 20, 30. Thus, in the medial side view in FIG. 7 it is possible to see the underside 40 of part of the curved, distal section 20 but not of the straight tail at the proximal end 30. The twist is also illustrated in FIG. 9, for example. This geometry allows the prosthesis 10 to more closely follow the trochlear ridge, so that the curved section follows the top of the ridge while the tail twists slightly around the bone, allowing better fixing of the prosthesis 10 and more effectively preventing lateral movement of the prosthesis 10 in use.

TABLE I

| Ridge Span RS | Height (h) | Width (w) | Fixed Screw 34 Length | Sliding Screw 34 Diameter | Sliding Screw 34 Length | Sliding Screw 34 Diameter | Example Dog Breed |
|---|---|---|---|---|---|---|---|
| 10 | 2 | 5 | 8 | 1.5 | 12 | 1.5 | 4 month old Chihuahua |
| 15 | 2.5 | 5 | 10 | 2 | 16 | 2 | Adult larger Chihuahua, smaller Westie |
| 20 | 3 | 6 | 12 | 2 | 20 | 2 | Westie, Beagle, Staffie |
| 25 | 3 | 7 | 14 | 2 | 24 | 2 | Adult Labrador, Staffie |
| 30 | 3.5 | 7 | 18 | 2 | 28 | 2 | Large Bulldog (33 Kg) |
| 35 | 4 | 7 | 20 | 2 | 32 | 2 | Large adult Rotweiler |
| 40 | 4 | 7 | 22 | 2 | 36 | 2 | Giant breeds: Bernese Mountain Dog |

The prosthesis 10 shown in the embodiment is suitable for attachment to the lateral side of a joint on a right leg or the medial side of a joint on the left leg. However, the present invention also provides another prosthesis 10 having mirrored geometry is also provided for attaching to the medial side of a joint on a right leg or the lateral side of a joint on a left leg.

Fitting the prosthesis 10 is very easy. First the ridge span RS of the trochlear ridge of the affected stifle joint is measured using a mediolateral radiograph as shown in FIG. 15, measuring from the level of the trochlear notch distally to the most proximal extent of the trochlear cartilage. The closest standard size prosthesis 10 for the appropriate side is then selected. In the case of FIG. 15 it can be seen that the ridge span RS of a mature, two year old Chihuahua is measured at 14.5 mm. If a veterinary surgeon were to implant a prosthesis 10 in this dog, based on the measurement he would select the 15 mm (RS 15) prosthesis kit shown in the table with the appropriately-sized prosthesis 10 and the accompanying fixed and sliding (distal and proximal) screws 24 34.

Next, a routine arthrotomy is performed on the stifle joint and the patella is dislocated. The prosthesis 10 is then positioned on the affected trochlear ridge 110 and a pilot hole of a prescribed diameter is then drilled through the round hole 22 just proximal to the trochlear notch 8b. The prescribed self-tapping titanium or other biocompatible distal screw 24 is then screwed through the round hole 22 into the bone to fix the distal end 20 of the prosthesis 10 to the trochlea. The screw size is prescribed based on the ridge span RS of the prosthesis 10 so that the end of the screw does not penetrate, or just minimally penetrates, the growth plate 7.

Next, another pilot hole of a prescribed diameter is drilled into the bone through the longitudinally extending slot (sliding hole) 32. Preferably, the hole is drilled in the region of the distal end of the slot 32, just proximal to the proximal end of the trochlear ridge 110. Although not apparent from FIG. 4A, it is preferable that the proximal screw 34 penetrates both cortices. It is not possible to definitively determine the correct size of the proximal screw 34 from X-rays alone because the screw 34 is at an angle and the caudal part of the bone 2 in the region where the proximal screw 34 is fixed becomes gradually thicker in the distal direction. Thus, it is not possible to determine from X-rays alone precisely how deep the screw 34 must be to engage the contra-lateral bone cortex. Accordingly, during surgery the depth of the hole is measured (as is done in normal surgery when a screw is applied to a bone) and a proximal screw 34 of the required size is selected and applied so the screw penetrates both cortices. It should be noted that there is no problem with the proximal screw 34 penetrating both cortices, even in a growing animal, as the bone will grow around it without inhibiting growth.

The intra-operative measurement of the hole depth and screw size for the proximal screw 34 to ensure both cortices are penetrated is fast and usually takes approximately five seconds. However, measurement of hole depth and screw size in this manner is preferably avoided for the distal screw 24 since it is strongly preferable to avoid any more than shallow penetration of the growth plate 7. The recognition by the inventor of the substantially constant geometry of the condyle and trochlea, and that this allows a predetermined distal screw size to be selected so that intra-operative measurement can be avoided, is therefore notable.

Although it will generally be possible to provide prosthesis kits with correctly sized distal and proximal screws 24, 34, in view of the difficulties in definitively determining the correct size of the proximal screw 34, prosthesis kits may also be provided only with the correctly sized distal screw 24, or with proximal screws 34 of a variety of sizes. In either case, the surgeon will select the appropriately sized proximal screw 34 during surgery.

The proximal screw 34 is not tightened fully, but so the screw head is just in contact with the prosthesis 10 and is countersunk so the screw head does not break the contour of the prosthesis 10.

The patella is then replaced and other necessary procedures such as tibial tuberosity transposition (TTT), and lateral imbrication are performed as required.

Generally speaking, the steps of actually fitting the prosthesis 10 will take an experienced veterinary surgeon under five minutes, but usually around 2 minutes. Accordingly, it can be seen that surgery to implant the prosthesis 10 is minimally traumatic in that it involves the application of only two screws, without sawing and chiseling the bone to deepen the trochlea groove or sawing off the trochlea entirely so that a complete prosthetic trochlea can be fitted. Thus, the procedure is less invasive and traumatic, and carries much less surgical risk, than wedge sulcoplasty (cutting a wedge to deepen the trochlear groove), block recession sulcoplasty (cutting a parallel-sided groove to deepen the trochlear groove), or a full artificial trochlea replacement. Moreover, there are minimal surgical risks in application and the prosthesis 10 is simple and very quick to apply. It is important to note that saving surgical time not only reduces costs, but also more importantly reduces anaesthetic risk and the risk of infection which has been shown to increase with the time the tissues are exposed.

In view of the simplicity of the procedure, success of the implant is less dependent on the skill of the surgeon. This has significant benefits in that more vets will be competent to fit the prosthesis 10 and there may be less need for the animal to go to a specialist referral centre to get treatment. Thus, the present invention has the significant benefit of opening up a low cost, easily obtained treatment option. Moreover since prostheses can be provided as kits of pre-scribed sizes and can be produced on a large scale with substantially constant geometry, the cost of an individual prosthesis can be minimised.

As noted above, because the prosthesis 10 is quick to apply and the procedure is minimally traumatic, infection and anaesthetic risks are minimised, and surgical time and money are also saved. For example, the prosthesis 10 is much quicker and cheaper to apply than a full trochlear prosthesis. In addition, the prosthesis 10 makes it possible to treat some mild grade I and grade II cases of luxation, which may not have been treated previously due to high risk versus relatively low benefit considerations. In other words, the lower risk versus the benefit obtained makes such treatment worthwhile where it would not be considered worthwhile using previous modes of treatment.

Moreover, due to the speed, simplicity and non-traumatic nature of the prosthesis 10 application, the veterinary surgeon cart decide to correct the trochlear ridge height deficiency much more readily and in more cases than as it stands at present with the current sulcoplasty procedures.

The prosthesis 10 in situ provides a consistent and adequate ridge height and provides an effective barrier sufficient to prevent luxation in most cases. The provision of the tail extends the height of the proximal ridge at the proximal end of the groove 120. This is particularly beneficial since it is in this area that the patella 130 is most likely to luxate, particularly where the animal has Patella Alta (an elongated patellar ligament).

In addition, although the steeply sloped medial side 60 of the prosthesis 10 acts to prevent luxation, should luxation nonetheless occur, the shallow slope of the lateral side 70 enables the patella 130 and patellar ligament to easily slip back over the prosthesis 10 into the trochlear groove 120.

Because the prosthesis 10 has a smooth, relatively low profile with no sharp edges, overlying soft tissue, the patella and the patellar ligament can slide over and alongside it without causing irritation.

Because the prosthesis 10 is suitably flexible and due to its geometry, it conforms comfortably to the shape of the trochlear ridge 110 and can be fitted in lag fashion. This combined with the fact that the longitudinal axes of the screws lie in non-parallel planes leads to a strong fitting of the prosthesis 10 with excellent resistance to lateral forces.

Depending on the trochlea of the suffering animal, it is possible to fit a prosthesis 10 to both trochlear ridges 110—that is, to fit a prosthesis 10 to either side of the trochlear groove 120. However, in the vast majority of cases it will be sufficient to fit a single prosthesis 10.

An important aspect of the present invention is that the prosthesis is suitable for fitting to immature animals. Because the proximal end 30 is formed as a tail with an elongated slot (sliding hole) 32 for the proximal screw 34, the prosthesis 10 can be fitted so that it spans the growth plate. By not fully tightening the proximal screw 34 but tightening it so that the screw head just touches the bottom of the countersunk portion, the screw 34 is able to slide along the elongated slot (sliding hole) 32 as the animal grows. As noted above, the length of the slot 32 is determined so that it provides sufficient travel for the screw as the animal matures to full growth. Moreover, the screws 24, 34 are sized and arranged so that they do not penetrate the growth plate 7. Consequently, implanting the prosthesis 10 in an immature animal corrects for trochlear abnormalities and helps keep the patella in the trochlear groove without hindering the growth of the femur.

Existing surgical techniques require the cutting of bone and so are not suitable for immature animals. Therefore the current ability to treat for patella luxation at an age when it would actually be the most desirable is limited to release and imbrication techniques only, which are not very effective on their own. Consequently the present invention provides a significant improvement on existing techniques.

The ability to implant the prosthesis 10 in immature animals is especially beneficial in that it avoids subsequent defects in growth and deformities. In particular, if the prosthesis 10 is fitted to an immature animal, this may prevent tibial rotation or torsion (varum/valgus); distal femoral torsion/rotation (genu varum/valgum); and decreased angle of the femoral neck with respect to the femur (Caxa Vara). Early fitting of the prosthesis 10 may also ensure that a sufficiently deep trochlear groove 120 is formed naturally by the patella 130 wearing the groove 120, and may resolve problems arising from Patella Alta. Because fitting the prosthesis 10 to immature animals may reduce the development of deformities, the incidence of cases where major corrective osteotomies will be needed in adulthood is also reduced.

As previously noted, where the patella 130 rides on the trochlear ridge 110 or is entirely luxated, this may result in exposure of subchondral bone and consequent pain. However, when fitted, the prosthesis 10 covers exposed subchondral bone and therefore reduces pain.

In addition, patella instability leads to chronic inflammation, which is a source of pain, and osteophyte formation, which can eventually reduce the range of motion of the joint. Left unchecked, these factors can eventually lead to degenerative joint disease, causing chronic pain and decreased range of motion. However, fitting the prosthesis 10 can substantially reduce or prevent all these symptoms, especially when the prosthesis 10 is fitted early.

In preferred embodiments, at least portions of the prosthesis 10 are radiopaque so the prosthesis 10 can be located and viewed using radiography. However even where the main body of the prosthesis 10 is radiolucent, titanium and other screws can be viewed by radiography, the top of the screw head indicating prosthesis height and proximal extension.

Although screws are preferred to anchor the prosthesis to the bone, any other suitable fixing means such as pins may also be used.

Although it is preferred that the prosthesis 10 is provided with a tail at its proximal end 30, it is possible to provide the prosthesis without a tail. In this case, the prosthesis ends at the end of the curved section. Preferably, the prosthesis is then sized so that it does not extend across the growth plate 7. Consequently an elongate slot 32 need not be provided and instead a single round hole may be provided at either end.

Even where a tail is provided at the proximal end 30 it is not necessary to provide an elongated slot 32 and a round hole may be provided instead. This arrangement is suitable where the prosthesis is fitted to an adult animal and no growth at the growth plate 7 is expected.

It is also possible to provide an elongated slot at both the distal and proximal ends 20, 30, or only at the distal end 30.

In addition, it is possible to provide more than one hole or slot at either or both ends of the prosthesis.

Although the prosthesis 10 has been described as being provided with an elongated slot 32, any suitable means may be provided for allowing the screws or other fixing means to move relative to one another as the bone grows. For example, the fixing means attached to the bone may be provided with a slot and the prosthesis may be provided with a protrusion to penetrate the elongated slot. Other mechanisms for allowing the prosthesis and the fixing means to slide or otherwise move relative to one another will be apparent to those skilled in the art and also within the ambit of the present invention. In particular, the prosthesis may be provided in two sliding or otherwise relatively moving parts so that the two fixing means can move relative to one another but not to the respective part of the prosthesis to which it is attached.

Although it is preferred that the body of the prosthesis 10 is made of UHMWPE, any biocompatible material with a suitable degree of flexibility may be used. Moreover, non-flexible metal or other material may also be used, especially in adult animals. Similarly, although it is preferred that the screws 24, 34 are made of titanium, other suitable biocompatible materials may be used.

In addition, the precise geometry of the prosthesis 10 may be varied as required, so long as the prosthesis 10 is suitably fitted to the trochlear ridge in situ.

Although the screws 24, 34 have been described as entities distinct from the prosthesis 10, it is possible to provide one or both screws 24, 34 as an integral part of the prosthesis 10 or to provide them in such a manner that they cannot be detached from the prosthesis 10.

The prosthesis 10 can be fitted to any animal (which term in this specification includes humans) but is especially suitable for four-legged animals, including equine and bovine mammals, as well as felines and canines.

Although a trochlear ridge prosthesis 10 has hitherto been described, the present invention also provides an implant of any suitable shape for fixing to a bone such that the implant spans a growth plate, or for implanting to span any growing part of an animal's anatomy. If attached to a bone, the bone need not be a femur and can be any bone of any animal. In this aspect of the invention, the implant is preferably fixed to span the growth plate or other growing part of the anatomy using two fixing means, such as pins. It should be noted that the fixing means need not be directly attached to a bone, so long as the implant can be held relative to the growth plate or other growing part in situ. Preferably, however, at least two screws are screwed into the bone to attach the implant.

Similarly to the above described prosthesis 10, the implant is provided with an elongated slot through which one of the fixing means can penetrate and along which the fixing means can slide as the bone or other part of the anatomy grows. The maximum amount of travel of the implant with respect to the fixing means is predetermined based on the expected growth of the bone or other growing part of the anatomy. If the implant is attached to abut the bone, it preferably sized and shaped to match the contour of the bone.

As with the prosthesis 10, any suitable means may be provided for allowing the screws or other fixing means to move relative to one another as the bone or other growing part grows.

The implant need not have prosthetic properties but may instead have a number of other functions, including without limitation eluting drugs, acting as a radiopaque marker for monitoring purposes and providing mechanical support for the bone or soft tissue.

The foregoing description has been given by way of example only and it will be appreciated by a person skilled in the art that modifications can be made without departing from the scope of the present invention.

The invention claimed is:

1. A trochlear ridge prosthesis for a canine or a feline having a femur and a femoral condyle, the prosthesis comprising:
   a curved section having a span RS from one end of the curved section to the other end with one of the ends being a proximal end, the curved section having a height RH being a maximum height of the curved section above the span, the height RH and the span RS being a ratio RH/RS of 0.23 to 0.27; and
   a tail extending from the proximal end of the curved section and the tail being straight for fitting over a portion of the femur extending from the femoral condyle of the canine or feline.

2. The trochlear ridge prosthesis according to claim 1, wherein a length of the tail is between 1 and 1.5 times the span.

3. The trochlear ridge prosthesis according to claim 1, further comprising a slot extending longitudinally along the tail for a fixing means for fixing the prosthesis to the canine or the feline, whereby the fixing means can slide in the slot.

4. The trochlear ridge prosthesis according to claim 3, wherein the fixing means is a screw comprising a screw head and the slot includes a countersink for accommodating the head of the fixing means.

5. The trochlear ridge prosthesis according to claim 1, further comprising a hole in the distal end of the curved section for a fixing means for fixing the prosthesis to the canine or the feline.

6. The trochlear ridge prosthesis according to claim 1, wherein an underside of the prosthesis is concave.

7. The trochlear ridge prosthesis according to claim 6, wherein an upper side of the prosthesis is convex, with a curvature of the concave underside being shallower than a curvature of the convex upper side.

8. The trochlear ridge prosthesis according to claim 1, wherein medial and lateral sides of the prosthesis are sloped, the slope of the medial side being steeper than the slope of the lateral side.

9. The trochlear ridge prosthesis according to claim 1, having a substantially smooth outer surface.

10. The trochlear ridge prosthesis according to claim 1, comprising at least two fixing means for fixing the prosthesis to a trochlear ridge, wherein the prosthesis is adapted so that said two fixing means are able to move relative to one another in situ.

11. A kit comprising a trochlear ridge prosthesis according to claim 1 and including at least one fixing means.

12. The kit according to claim 11, comprising one or both of a cancellous screw for mounting a distal end and a cortical screw for mounting a proximal end.

13. The trochlear ridge prosthesis according to claim 1, wherein the canine or feline has a trochlear ridge and the prosthesis has an underside that is concave and configured to abut the trochlear ridge.

* * * * *